US011771691B2

(12) United States Patent
Daud et al.

(10) Patent No.: US 11,771,691 B2
(45) Date of Patent: Oct. 3, 2023

(54) PHARMACEUTICAL COMPOSITION OF TAMSULOSIN AND DUTASTERIDE

(71) Applicant: ZIM LABORATORIES LIMITED, Nagpur (IN)

(72) Inventors: Anwar Daud, Nagpur (IN); Girish Achliya, Nagpur (IN); Nitin Maski, Nagpur (IN); Shashikant Wadle, Nagpur (IN)

(73) Assignee: ZIM LABORATORIES LIMITED, Nagpur (IN)

( * ) Notice: Subject to any disclaimer, the term of this patent is extended or adjusted under 35 U.S.C. 154(b) by 0 days.

(21) Appl. No.: 17/057,093

(22) PCT Filed: May 20, 2019

(86) PCT No.: PCT/IN2019/050403
§ 371 (c)(1),
(2) Date: Nov. 19, 2020

(87) PCT Pub. No.: WO2019/224840
PCT Pub. Date: Nov. 28, 2019

(65) Prior Publication Data
US 2021/0186951 A1    Jun. 24, 2021

(30) Foreign Application Priority Data
May 19, 2018    (IN) .............................. 201821018849

(51) Int. Cl.
| | | |
|---|---|---|
| *A61K 31/473* | (2006.01) | |
| *A61K 9/50* | (2006.01) | |
| *A61K 31/18* | (2006.01) | |
| *A61K 9/48* | (2006.01) | |
| *A61K 9/16* | (2006.01) | |
| *A61K 9/20* | (2006.01) | |

(52) U.S. Cl.
CPC .......... *A61K 31/473* (2013.01); *A61K 9/1694* (2013.01); *A61K 9/2081* (2013.01); *A61K 9/4808* (2013.01); *A61K 9/4858* (2013.01); *A61K 9/4866* (2013.01); *A61K 9/501* (2013.01); *A61K 9/5015* (2013.01); *A61K 9/5026* (2013.01); *A61K 9/5047* (2013.01); *A61K 9/5073* (2013.01); *A61K 31/18* (2013.01)

(58) Field of Classification Search
CPC ................ A61K 31/473; A61K 9/1694; A61K 9/2081; A61K 9/4808; A61K 9/4858; A61K 9/4866; A61K 9/501; A61K 9/5015; A61K 9/5026; A61K 9/5047; A61K 9/5073; A61K 31/18; A61K 31/58
See application file for complete search history.

(56) References Cited

U.S. PATENT DOCUMENTS

| | | |
|---|---|---|
| 2006/0204588 A1 | 9/2006 | Liversidge |
| 2011/0244033 A1 | 10/2011 | Johannes |
| 2016/0074333 A1 | 3/2016 | Dabre et al. |

FOREIGN PATENT DOCUMENTS

| | | |
|---|---|---|
| EP | 2468262 A1 | 6/2012 |
| WO | 2006055659 | 5/2006 |
| WO | 2012127495 | 9/2012 |
| WO | 2016003180 A1 | 1/2016 |
| WO | WO-2018102526 A1 * | 6/2018 |

OTHER PUBLICATIONS

Fossler, M.J.; Collins, D.A .; Thompson, M. M; Nino, A.; Bianco, J.J.; Chetty, D. Pharmacokinetic Bioquivalence Studies of a Fixed-Dose Combination of Tamsulosin and Dutasteride in Healthy Volunteers. Clin. Drug Invest., 34, 5, 33-349. (Year: 2014).*

Dinggeng He et al., "Core-shell particles for controllable release of drug", Chemical Engineering Science 2015, vol. 125, Mar. 24, 2015, pp. 108-120, https://doi.org/10.1016/j.ces.2014.08.007.

* cited by examiner

*Primary Examiner* — Jessica Worsham
(74) *Attorney, Agent, or Firm* — Maschoff Brennan

(57) ABSTRACT

The present invention relates to a novel pharmaceutical composition of Tamsulosin and Dutasteride and process of manufacture thereof. Specifically, the present invention relates to multiparticulate(s) of Tamsulosin and Dutasteride filled in capsule or/compressed in tablet dosage form and process of manufacture thereof.

13 Claims, No Drawings

PHARMACEUTICAL COMPOSITION OF TAMSULOSIN AND DUTASTERIDE

FIELD OF THE INVENTION

The present invention relates to a novel pharmaceutical composition of Tamsulosin and Dutasteride and process of manufacture thereof. Specifically, the present invention relates to multiparticulate(s) of Tamsulosin and Dutasteride filled in capsule dosage form or tableting in tablet form and process of manufacture thereof.

BACKGROUND OF THE INVENTION

Tamsulosin is α-IA adrenergic receptor antagonist. Chemically Tamsulosin is (-)—(R)-5-[2-[[2-(o-Ethoxyphenoxy) ethyl]amino]propyl]-2-methoxybenzenesulfonamide, monohydrochloride. The empirical formula of tamsulosin hydrochloride is $C_{20}H_{28}N_2O_5S \cdot HCl$ and molecular weight of tamsulosin hydrochloride is 444.97. Its structural formula is represented in FIG. 1.

FIG. 1

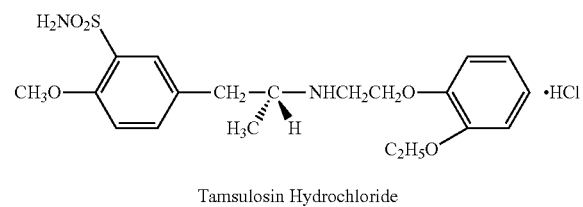

Tamsulosin Hydrochloride

Dutasteride is a synthetic 4-azasteroid compound. It is chemically designated as (5α,17β)-N-{2,5bis(trifluoromethyl)phenyl}-3-oxo-4-azaandrost-1-ene-17-carboxamide. The empirical formula of dutasteride is $C_{27}H_{30}F_6N_2O_2$, and molecular weight is 528.5. Its structural formula is represented in FIG. 2.

FIG. 2

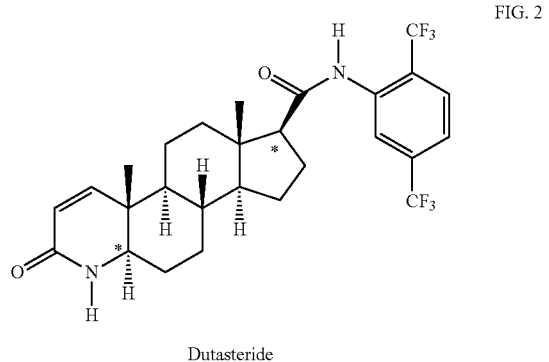

Dutasteride

Tamsulosin hydrochloride and Dutasteride is marketed in combination in the form of hard gelatin capsule in which Tamsulosin hydrochloride is in the form of sustained release pellets which are filed in hard gelatin capsule, whereas Dutasteride is the form of immediate release soft gelatin capsule which is filed in hard gelatin capsule along with Tamsulosin SR pellets. Tamsulosin hydrochloride and Dutasteride is marketed under JALYN trademark in USA and COMBODART trademark in UK.

Currently marketed, JALYN and COMBODART, i.e., innovator products (Tamsulosin and Dutasteride capsule) utilizing capsule technology which is quite complex, time consuming and expensive.

Some of the prior-art documents disclosing Tamsulosin and Dutasteride composition/formulation are given below:

WO2016003180 discloses a capsule dosage form of Tamsulosin and Dutasteride where Tamsulosin containing Pellets are filled in Hard capsule. Said Hard capsule is then coated with Dutasteride containing component.

WO2012127495 discloses a pharmaceutical composition comprising, an inner core; a coating layer comprising insoluble 5-alpha-reductase inhibitor as an active ingredient; and optionally, a colouring layer and process for the pharmaceutical preparation thereof, wherein insoluble 5-alpha-reductase inhibitor is Dutasteride.

US2006204588 describes nanoparticulate compositions having an effective average particle size of less than about 2000 nm of finasteride, dutasteride, tamsulosin hydrochloride, or a combination thereof. The formulations exhibit unexpectedly prolonged release and can be maintained in a depot for release to a patient for a period of up to six months.

US20110244033 discloses a combination dosage form comprising a dose of tamsulosin physically separated from a dose of a testosterone-5a-reductase inhibitor (dutasteride), said combination dosage form comprising an inner capsule loaded with said dose of testosterone-5a-reductase inhibitor and an outer capsule surrounding the inner capsule and forming a space between the inner and outer capsules, wherein the space between the inner capsule and outer capsule is filled with said tamsulosin dose in the form of a population of tamsulosin pellets comprising tamsulosin hydrochloride uniformly dispersed in a carrier matrix.

WO2006055659 discloses a fixed dose combination comprising: dutasteride; and tamsulosin, wherein the dutasteride is provided in the form of a softgel and the tamsulosin is provided in the form of beads, and further wherein the dutasteride and tamsulosin are filled into a capsule.

Yet there is unmet need for providing simple, cost effective and high speed technology for development of Tamsulosin and Dutasteride combined composition.

The present invention identified complexity in marketed technology, and disclosing Tamsulosin and Dutasteride combined composition overcoming limitations of the prior-art documents.

None of the cited reference teaches a suitable composition of capsule dosage form comprising Tamsulosin and Dutasteride in single unit of multiparticulate filled in Capsule.

The present applicant invented novel composition/formulation of Tamsulosin and Dutasteride in single pellet (multiparticulate) which are filled in hard gelatin Capsule as compared to currently marketed formulation.

OBJECTIVE OF THE INVENTION

A main object of the present invention is to prepare multiparticulate(s) of Tamsulosin and Dutasteride.

Another object of the present invention is to prepare a capsule dosage form comprising multiparticulate(s) of Tamsulosin and Dutasteride where Tamsulosin and Dutasteride are present in single unit.

Another object of the present invention is to provide a capsule dosage form comprising multiparticulate(s) of Tamsulosin and Dutasteride where plurality of physically separated Tamsulosin units and Dutasteride units are present.

Another object of the present invention is to provide a pellet formulation of Tamsulosin and Dutasteride which are further filled in a capsule or tableting in tablet form.

SUMMARY OF THE INVENTION

In an aspect of the present invention, the present invention discloses a process for the preparation of a multiparticulate formulation, comprising the step of: a) preparing inner core of Tamsulosin to obtain modified release; b) optionally, coating an modified release polymer coating dispersion on said inner core to obtain modified release inner core; c) optionally, coating said modified release inner core with first seal coating solution to obtain first seal coated core; d) coating said inner core or modified release coated inner core, or first seal coated inner core with outer coating dispersion of dutasteride to obtain dutasteride coated inner core; e) optionally, coating said dutasteride coated inner core with second seal coating dispersion to obtain the multiparticulate formulation.

In another aspect of the present invention, the present invention discloses a process for the preparation of a multiparticulate formulation, comprising the step of: a) preparing inner core of Tamsulosin; b) optionally, coating an modified release polymer coating dispersion on said inner core to obtain modified release inner core; c) optionally, coating said inner core or modified release inner core with first seal coating solution to obtain first seal coated core; d) coating said inner core or modified release coated inner core, or first seal coated inner core with outer coating dispersion of dutasteride to obtain dutasteride coated inner core; e) optionally, coating said dutasteride coated inner core with second seal coating dispersion to obtain the multiparticulate formulation.

In one another aspect of the present invention, the present invention discloses a process for the preparation of a multiparticulate formulation, comprising the step of: a) preparing inner core of Tamsulosin to obtain modified release; b) coating an modified release polymer coating dispersion on said inner core to obtain modified release inner core; c) coating said modified release inner core with first seal coating solution to obtain first seal coated core; d) coating said inner core or modified release coated inner core, or first seal coated inner core with outer coating dispersion of dutasteride to obtain dutasteride coated inner core; e) coating said dutasteride coated inner core with second seal coating dispersion to obtain the multiparticulate formulation.

In an embodiment of the present invention, preparing inner core of Tamsulosin comprises the step of: i) dry mixing tamsulosin with at least one diluent and at least one antioxidant or one or more pharmaceutically acceptable excipient(s) to obtain a mixture; ii) preparing wet mass of said mixture with a binder solution; iii) granulating or pelleting or extruding said wet mass to obtain granules or pellets or extrudates; iv) spheronizing said granules or pellets or extrudates to obtain spheronized granules or pellets or extrudates; v) drying the spheronized granules or pellets or extrudates.

In an embodiment of the present invention, the modified release coating dispersion preparation process comprises of: dispersing release modifying agent, plasticizer and anti-tacking agent, optionally one or more pharmaceutically acceptable excipient(s) in a processing solvent to obtain a homogenous dispersion for the modified release coating.

In an embodiment of the present invention, the first seal coating solution preparation process comprises of: i) dispersing seal coating polymer in a first processing solvent followed by addition of second processing solvent; ii) stirring said dispersion continuously to obtain a clear solution; iii) adding plasticizer, optionally one or more pharmaceutically acceptable excipient(s) to said clear solution to obtain first seal coating solution.

In an embodiment of the present invention, the outer coating dispersion preparation process comprises of: i) dispersing dutasteride in a first processing solvent with continuous stirring; ii) adding binder, antioxidant, solubilizer, anti-tacking, emulsifying agent, optionally one or more pharmaceutically acceptable excipient(s) to said dispersion to obtain a homogenous outer coating dispersion.

In an embodiment of the present invention, the second seal coating dispersion preparation process comprises of: i) dispersing seal coating polymer in a first processing solvent followed by addition of second processing solvent; ii) adding plasticizer, anti-tacking agent, opacifier, coloring agent, optionally one or more pharmaceutically acceptable excipient(s) with continuous stirring to obtain a homogenous second seal coating dispersion.

In still another aspect of the present invention, the present invention discloses a multiparticulate formulation, comprising: a) an inner core of Tamsulosin; and b) an outer coating layer of Dutasteride.

In an embodiment of the present invention, the inner core is coated with modified release coating.

In an embodiment of the present invention, the modified release coating is coated with first seal coating.

In an embodiment of the present invention, wherein the inner core comprises: a) tamsulosin or its hydrochloride salt; b) diluent; c) antioxidant; d) binder solution; e) optionally, one or more pharmaceutically acceptable excipient(s).

In an embodiment of the present invention, the binder solution comprises: a) release modifying agent; b) plasticizer, c) surfactant; d) processing solvent; e) optionally, one or more pharmaceutically acceptable excipient(s).

In an embodiment of the present invention, the modified release coating comprises: a) release modifying agent; b) plasticizer; c) anti-tacking agent; d) processing solvent; e) optionally, one or more pharmaceutically acceptable excipient(s).

In an embodiment of the present invention, the first seal coating comprises: a) seal coating polymer, b) plasticizer; c) one or more processing solvent(s); d) optionally, one or more pharmaceutically acceptable excipient(s).

In an embodiment of the present invention, the outer coating layer comprises: a) dutasteride; b) antioxidant; c) binder; d) emulsifying agent; e) processing solvent; f) optionally, one or more pharmaceutically acceptable excipient(s).

In an embodiment of the present invention, the outer coating layer is coated with second seal coating.

In an embodiment of the present invention, the second seal coating comprises: a) seal coating polymer; b) plasticizer; c) anti-tacking agent; d) opacifier; e) coloring agent; f) processing solvent; g) optionally, one or more pharmaceutically acceptable excipient(s).

In an embodiment of the present invention, the formulation is in the form of pellets, granules or extrudates.

In an embodiment of the present invention, the pellets are filled in a capsule, preferably in a hard gelatin capsule or compressed/tableting in a tablet form.

In an embodiment of the present invention, the tamsulosin is tamsulosin hydrochloride.

In an embodiment of the present invention, the diluent is selected from the group consisting of mannitol, talc, magnesium stearate, sodium chloride, potassium chloride, citric acid, spray-dried lactose, hydrolyzed starches, directly compressible starch, microcrystalline cellulose, cellulosics polymer, sugar alcohols (like sorbitol, xylitol and others), sucrose, sucrose-based materials, calcium sulfate, dibasic calcium phosphate and dextrose, fructose, or combination thereof and alike.

In an embodiment of the present invention, the antioxidant is selected from the group consisting of alkyl gallates (e.g. dodecyl-, ethyl-, octyl-, propyl-gallate), butylated hydroxyanisole, butylated hydroxytoluene, tocopherols (e.g. alpha tocopherol), ascorbic acid palmitate, ascorbic acid, sodium ascorbate, potassium and sodium salts of Sulphurous acid (e.g. bisulphites, metabisulphites, Sulphites), flavonoides (rutin, quercetin) or combination thereof and alike.

In an embodiment of the present invention, the release modifying agent is selected from the group consisting of acrylate polymers, acrylate or/methacrylate copolymer(s), povidone derivatives, cellulose derivatives (hydroxypropylcellulose, hydroxypropylmethylcellulose, ethyl cellulose, or other cellulose derivatives), or combination thereof and alike.

In an embodiment of the present invention, the plasticizer is selected from the group consisting of polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate or combination thereof and alike.

In an embodiment of the present invention, the surfactant is selected from the group consisting of polysorbate and its derivatives, sodium lauryl sulfate, poloxamer, sucrose monostearate, sucrose monolaurate and sucrose monopalmitate or combination thereof and alike.

In an embodiment of the present invention, the anti-tacking agent is selected from the group consisting of purified talc, silica, magnesium Stearate, stearic acid, glyceryl monostearate, sodium stearyl fumerate, hydrogenated oils, polyethylene glycols, sodium stearate or combination thereof and alike.

In an embodiment of the present invention, the seal coating polymer is selected from the group consisting of polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates or combination thereof and alike.

In an embodiment of the present invention, binder may be dry or wet, further the binder is selected from the group consisting of matrix binders (dry starch, dry sugars), film binders (PVP, starch paste, celluloses, bentonite, sucrose), and chemical binders (polymeric cellulose derivatives, such as carboxy methyl cellulose, HPC and HPMC; sugar syrups; corn syrup; water soluble polysaccharides such as acacia, tragacanth, guar and alginates; gelatin; gelatin hydrolysate; agar, sucrose; dextrose; and non-cellulosic binders, such as PVP, PEG, vinyl pyrrolidone copolymers, pregelatinized starch, sorbitol, and glucose) or combination thereof and alike.

In an embodiment of the present invention, the emulsifying agent is selected from the group consisting of polyoxy hydrogenated castor oil or its derivatives, acacia, lecithin, tragacanth, Agar, pectin, sodium lauryl sulfate, sodium dioctyl sulfosuccinate or combination thereof and alike.

In an embodiment of the present invention, the opacifier is selected from the group consisting of titanium dioxide, zinc oxide, calcium carbonate, talc, aluminum silicate, magnesium carbonate, calcium sulfate and aluminum hydroxide or combination thereof and alike.

In an embodiment of the present invention, the coloring agent is selected from the group consisting of titanium dioxide, food dyes, lakes, natural vegetable colorants, iron oxides, silicates, sulfates, magnesium hydroxide and aluminum hydroxide or combination thereof and alike. Colour approved by D& C act and Soluble synthetic dye (coaltar dyes) and insoluble dyes (iron oxide) or combination thereof and alike.

In an embodiment of the present invention, processing solvent includes but not limited to aqueous or non-aqueous, the processing solvent is selected from the group consisting of water, isopropyl alcohol, ethanol, acetone, methanol, and dichloromethane. or combination thereof and alike.

In an embodiment of the present invention, the first processing solvent or second processing solvent can be same or different.

DETAILED DESCRIPTION OF THE INVENTION

While the invention has been described and illustrated with reference to certain embodiments thereof, those skilled in the art will appreciate that various adaptations, changes, modifications, substitutions, deletions, or additions of procedures and protocols may be made without departing from the spirit and scope of the invention. The present invention can be more readily understood by reading the following detailed description of the invention and study of the included examples. As used herein, the term "composition", is intended to encompass at least one active ingredient, and the other inert ingredient(s) (acceptable excipients). Such compositions, depending upon the context, are also synonymous with "formulation" and "dosage form". These formulations/composition may be prepared in any form, such as solid and liquid dosage form. The solid dosage form can include oral dosage form (powder, tablet, capsule, soft capsule, aqueous medicine, pill, powder, sachet, granule and pellet) and liquid formulation can include solution, suspension, emulsion, syrup, elixirs, etc.

The composition of the present invention can also be in the form of pharmaceutical compositions or dosages, and pharmaceutical dosage forms may be used in the form of their pharmaceutically acceptable salts, and also may be used alone or in appropriate association, as well as in combination with other pharmaceutically active compounds. The desirable dose of the inventive composition varies depending on the condition and the weight of the subject, severity, drug form, route and period of administration, and may be chosen by those skilled in the art.

The term "excipient" means a pharmacologically inactive component such as a diluent, lubricant, surfactant, carrier, or the like. The excipients that are useful in preparing a pharmaceutical composition are generally safe, non-toxic and are acceptable for human as well as veterinary pharmaceutical use. Reference to an excipient includes both one and more than one such excipient. Co-processed excipients are also covered under the scope of the present invention.

The term "dosage" is intended to encompass a formulation expressed in terms of mg/kg/day. The dosage is the amount of an ingredient administered in accordance with a particular dosage regimen. A "dose" is an amount of an agent administered to a subject in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or/doses of the formulation. The particular meaning in any case will be apparent from context.

The term "Diluent" herein refers to as (also referred to as filler, dilutant or thinner) a diluting agent. Diluents are low-molecular-weight, low-viscosity compounds that are used to reduce the viscosity or enhance the solubility of a resin and/or hardener. Diluents may be either reactive or non-reactive. As inactive ingredients, they are added to tablets and capsules in addition to the active drug. Diluents act as fillers in pharmaceutical tablets/pellets/granules to increase weight and improve content uniformity. Natural diluents include starches, hydrolyzed starches, and partially pregelatinized starches. Common diluents include microcrystalline cellulose, anhydrous lactose, lactose monohydrate, sugar alcohols such as sorbitol, xylitol, mannitol and other pharmaceutically acceptable diluents or mixture thereof and alike.

The term "Antioxidant" herein refers to those compounds that inhibit oxidation and may be added for this purpose to various pharmaceutical products subject to deterioration by oxidative processes.

The term "Release Modifying Agent" herein refers to describe products that alter the timing and/or the rate of release of the drug substance. These agents are designed to release a drug slowly or delayed over an extended period of time. Formulations must be robust to ensure drug release over time and avoid dose-dumping.

"Plasticizer(s)" are used mainly for oral solid dosage forms. Plasticizers are added to the polymers used as film forming agents in order to make the polymer pliable and soft, enhancing the flexibility and plasticity of the films. They are added to these products to reduce the glass transition temperature facilitating the thermal stability of the drug and other ingredients.

"Surfactants" are widely used in formulating new and in modifying existing medical preparations, in the production of proprietary medicines, in the production of chemical preparation. The functional role of surfactants in pharmaceutical preparations include: modulating solubility and bioavailability of APIs; increasing the stability of active ingredients in the dosage forms; helping active ingredients to maintain preferred polymorphic forms; maintaining the pH and/or osmolality of liquid formulations; and modulating immunogenic responses of active ingredients.

"Anti-tacking Agent" is a necessary component in a coating system to prevent tackiness of the dosage forms during the manufacturing process. Commonly, talc was chosen as anti-tacking agent.

"Seal Coating Polymer" herein refers to as a polymer, used to prevent interaction between two layers.

"Binder" are formulated to act as an adhesive to literally "bind together" powders, granules and other dry ingredients to impart to the product the necessary mechanical strength. They can also give volume to low active dose tablets. Commonly used in wet granulation, binders are added to create a more effective and predictable granule formation. Binders are classified according to their application.

"Emulsifying Agent(s)" are liquid preparations that typically contain a mixture of oil and water. The oil and water mixture is kept homogenized by the addition of an emulsifying agent. Excipients ensure that the oil phase is kept finely dispersed throughout the water as minute globules.

"Opacifier(s)" are used to give more pastel color and increase film coverage. They can provide white coat or mask the color of the tablet/pellet/granule core. These are mostly inorganic material. The substances employed are—Titanium dioxide (most commonly used), Talc, Aluminum silicate, Magnesium carbonate, Calcium sulfate, Aluminum hydroxide, other pharmaceutically acceptable opacifier(s) or mixture thereof and alike.

"Processing Solvent(s)" or "Solvent(s)' can serve one or more functions in pharmaceutical manufacture or formulation. Solvents are chemical substances that can dissolve, suspend or extract other materials usually without chemically changing either the solvents or the other materials. Solvents can be organic or inorganic. They are used to enhance solubility, taste, anti-microbial effectiveness or stability, to reduce dose volume or to optimize insolubility. Solvents are also used to help the final product in achieving proper consistency.

"Coloring Agent(s)" are used to impart a distinctive appearance to a formulation or dosage form. They are non-toxic, free from impurities and have not physiological effect.

The "other" pharmaceutically acceptably excipients, if present, are generally used to provide proper characteristics of the composition for the pelletization procedure.

The pellet cores of the present invention can be made by various known techniques. The main techniques are, e.g., high shear pelletization, fluid bed pelletization, hot-melt and extrusion-spheronization. Suitable equipment for producing pellet cores for the product of the invention comprises high-shear mixer/granulators. Alternate pelletization techniques, as known in the prior art, are suitable as well.

The term "modified release" as used herein refers to formulation or dosage units of this invention that are slowly or/delayed and continuously release or/dissolved and absorbed in the stomach and gastrointestinal tract over a period of time.

Modified release pharmaceutical dosage forms have long been used to optimize drug delivery, enhance patient compliance, maintaining uniform/substantially constant plasma concentration of drug without much fluctuation in plasma concentration and decrease more consumption or/toxicity of drug especially by reducing the number of doses of medicine the patient must take in a day. In some instances, it is also desirable for a dosage form to deliver more than one drug(s) at different or same rates or times in combination in single formulation/dosage form. Modified release dosage forms should ideally be adaptable so that release rates and profiles can be matched to physiological and chrono-therapeutic requirements. Because the onset and duration of the therapeutic efficacy of drugs vary widely, as do their absorption, distribution, metabolism, and elimination, it is often desirable to modify the release of different drugs in different ways, or to have a first dose of drug (active ingredient) immediately released from the dosage form, while a second dose of the same or a different drug is released in a modified, e.g. delayed, pulsatile, repeat action, controlled, sustained, prolonged, extended, or retarded manner.

In an aspect of the present invention, the present invention discloses a process for the preparation of multiparticulate formulation, comprising the step of: a) preparing inner core of Tamsulosin; b) optionally, coating an modified release (MR) coating dispersion on said inner core to obtain MR coated inner core; c) optionally, coating said MR coated inner core with first seal coating solution to obtain first seal coated core; d) coating said inner core or MR coated inner core, or first seal coated inner core with outer coating dispersion of dutasteride to obtain dutasteride coated inner core; e) optionally, coating said dutasteride coated inner core with second seal coating dispersion to obtain the multiparticulate formulation.

In one feature of the present invention, preparing inner core of Tamsulosin comprises the step of: i) dry mixing tamsulosin with at least one diluent and at least one antioxidant, optionally one or more pharmaceutically acceptable excipient(s) to obtain a mixture; ii) preparing wet mass of said mixture with a binder solution; iii) granulating or pelleting or extruding said wet mass to obtain granules or pellets or extrudates; iv) spheronizing said granules or pellets or extrudates to obtain spheronized granules or pellets or extrudates; v) drying the spheronized granules or pellets or extrudates, and passing through suitable screen to obtain inner core of Tamsulosin.

In one feature of the present invention, the modified release coating dispersion preparation process comprises of: dispersing release modifying agent, plasticizer, anti-tacking agent or optionally one or more pharmaceutically acceptable excipient(s) in a processing solvent to obtain a homogenous dispersion for the modified release coating.

In one feature of the present invention, the first seal coating solution preparation process comprises of: i) dispersing seal coating polymer in a first processing solvent followed by addition of second processing solvent; ii) stirring said dispersion continuously to obtain a clear solution; iii) adding plasticizer to said clear solution to obtain first seal coating solution.

In one feature of the present invention, the outer coating dispersion preparation process comprises of: i) dispersing dutasteride in a first processing solvent with continuous stirring; ii) adding binder, antioxidant, solubilizer, anti-tacking, emulsifying agent, optionally one or more pharmaceutically acceptable excipient(s) to said dispersion to obtain a homogenous outer coating dispersion.

In one feature of the present invention, the second seal coating dispersion preparation process comprises of: i) dispersing seal coating polymer in a first processing solvent followed by addition of second processing solvent; ii) adding plasticizer, anti-tacking agent, opacifier, coloring agent, optionally one or more pharmaceutically acceptable excipient(s) with continuous stirring to obtain a homogenous second seal coating dispersion.

In another aspect of the present invention, the present invention discloses a multiparticulate formulation, comprising: a) an inner core of Tamsulosin; and b) an outer coating layer of Dutasteride. In one feature of the present invention, the inner core is coated with modified release coating layer.

In one feature of the present invention, the modified release coating layer is coated with first seal coating.

In one feature of the present invention, the inner core comprises: a) 0.1-0.5 wt % of tamsulosin; b) 50-95 wt % of diluent; c) 0.1-0.5 wt % of antioxidant; d) 1-20 wt % of binder solution, optionally one or more pharmaceutically acceptable excipient(s).

In one feature of the present invention, the binder solution comprises: a) 1-20 wt % of release modifying agent; b) 0.1-5.0 wt % of plasticizer, c) 0.1-0.5 wt % of surfactant; and d) processing solvent, optionally one or more pharmaceutically acceptable excipient(s).

In one feature of the present invention, the modified release coating comprises: a) 1-20 wt % of release modifying agent; b) 0.1-0.5 wt % of plasticizer, c) 0.1-2.0 wt % of anti-tacking agent; d) processing solvent, optionally one or more pharmaceutically acceptable excipient(s).

In one feature of the present invention, the first seal coating comprises: a) 1-5 wt % of seal coating polymer, b) 0.1-5 wt % of plasticizer; c) one or more processing solvent(s), optionally one or more pharmaceutically acceptable excipient(s).

In one feature of the present invention, the outer coating layer comprises: a) 0.1-0.5 wt % of dutasteride; b) 0.01-2.0 wt % of antioxidant; c) 1-5 wt % of binder, d) 0.1-0.5 wt % of solubilizer e) 0.1-2.0 wt % of anti-tacking agent f) 0.1-0.5 wt % of emulsifying agent; and g) processing solvent, optionally one or more pharmaceutically acceptable excipient(s).

In one feature of the present invention, the outer coating layer is coated with second seal coating.

In one feature of the present invention, the second seal coating comprises: a) 0.5-5 wt % of seal coating polymer; b) 0.1-0.5 wt % of plasticizer, c) 0.1-2.0 wt % of anti-tacking agent; d) 0.1-5.0 wt % of opacifier, e) 0.01-2.0 wt % of coloring agent; and f) processing solvent, optionally one or more pharmaceutically acceptable excipient(s).

In one feature of the present invention, the formulation is in the form of pellets, granules or extrudates.

In one feature of the present invention, the pellets are filled in a capsule, preferably in a hard gelatin capsule or compressed in tablet form.

In one feature of the present invention, the diluent is selected from the group consisting of mannitol, talc, magnesium stearate, sodium chloride, potassium chloride, citric acid, spray-dried lactose, hydrolyzed starches, directly compressible starch, microcrystalline cellulose, cellulosics polymer, sugar alcohols (like sorbitol, xylitol and others), sucrose, sucrose-based materials, calcium sulfate, dibasic calcium phosphate and dextrose, fructose, or combination thereof and alike.

In one feature of the present invention, the antioxidant is selected from the group consisting of alkyl gallates (e.g. dodecyl-, ethyl-, octyl-, propyl-gallate), butylated hydroxyanisole, butylated hydroxytoluene, tocopherols (e.g. alpha tocopherol), ascorbic acid palmitate, ascorbic acid, sodium ascorbate, potassium and sodium salts of Sulphurous acid (e.g. bisulphites, metabisulphites, Sulphites), flavonoides (rutin, quercetin) or combination thereof and alike.

In one feature of the present invention, the release modifying agent is selected from the group consisting of acrylate polymers, acrylate or/methacrylate copolymer(s), povidone derivatives, cellulose derivatives (hydroxypropylcellulose, hydroxypropylmethylcellulose, ethyl cellulose, or other cellulose derivatives), or combination thereof and alike.

In one feature of the present invention, the plasticizer is selected from the group consisting of polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate or combination thereof and alike.

In one feature of the present invention, the surfactant is selected from the group consisting of polysorbate and its derivatives, sodium lauryl sulfate, poloxamer, sucrose monostearate, sucrose monolaurate and sucrose monopalmitate or combination thereof and alike.

In one feature of the present invention, the anti-tacking agent is selected from the group consisting of purified talc, silica, magnesium Stearate, stearic acid, glyceryl monostearate, sodium stearyl fumerate, hydrogenated oils, polyethylene glycols, sodium stearate or combination thereof and alike.

In one feature of the present invention, the seal coating polymer is selected from the group consisting of polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates or combination thereof and alike.

In one feature of the present invention, binder may be dry or wet, further the binder is selected from the group consisting of matrix binders (dry starch, dry sugars), film binders (PVP, starch paste, celluloses, bentonite, sucrose), and chemical binders (polymeric cellulose derivatives, such as carboxy methyl cellulose, HPC and HPMC; sugar syrups; corn syrup; water soluble polysaccharides such as acacia, tragacanth, guar and alginates; gelatin; gelatin hydrolysate; agar, sucrose; dextrose; and non-cellulosic binders, such as PVP, PEG, vinyl pyrrolidone copolymers, pregelatinized starch, sorbitol, and glucose) or combination thereof and alike.

In one feature of the present invention, the emulsifying agent is selected from the group consisting of polyoxy hydrogenated castor oil or its derivatives, acacia, lecithin, tragacanth, Agar, pectin, sodium lauryl sulfate, sodium dioctyl sulfosuccinate or combination thereof and alike.

In one feature of the present invention, the opacifier is selected from the group consisting of titanium dioxide, zinc oxide, calcium carbonate, talc, aluminum silicate, magnesium carbonate, calcium sulfate and aluminum hydroxide or combination thereof and alike.

In one feature of the present invention, the coloring agent is selected from the group consisting of titanium dioxide, food dyes, lakes, natural vegetable colorants, iron oxides, silicates, sulfates, magnesium hydroxide and aluminum hydroxide or combination thereof and alike. Colour approved under Drug & Cosmetic act, soluble synthetic dye (coal tar dyes) and insoluble dyes (iron oxide) or combination thereof and alike.

In one feature of the present invention, processing solvent includes but not limited to aqueous or non-aqueous, and is selected from the group consisting of water, isopropyl alcohol, ethanol, acetone, methanol, and dichloromethane or combination thereof and alike. In one feature of the present invention, the first processing solvent or second processing solvent can be same or different.

In one feature of the present invention, the tamsulosin is tamsulosin hydrochloride.

Some illustrative non-limiting examples of the present invention are described below.

EXAMPLES

Example 1

Tamsulosin HCl 0.4/Dutasteride 0.5 mg Capsule Formulation a) Composition of Tamsulosin Hydrochloride and Dutasteride Pellets

| Sr. No. | Ingredients | % (Range) |
|---|---|---|
| 1. | Tamsulosin Hydrochloride | 0.1-0.5 |
| 2. | Microcrystalline Cellulose (MCC) | 50-95 |
| 3. | Butylated Hydroxy Toluene (BHT) | 0.1-0.5 |
| 4. | Propyl Gallate (PG) | 0.1-0.5 |
| 5. | Methacrylic Acid and Ethyl Acrylate Copolymer | 1-20 |
| 6. | Triethyl Citrate | 0.1-5.0 |
| 7. | Polysorbate 80 | 0.1-0.5 |
| 8. | Purified Water | q.s. |
| 9. | Methacrylic Acid and Ethyl Acrylate Copolymer | 1-20 |
| 10. | Triethyl Citrate | 0.1-0.5 |
| 11. | Purified Talc | 0.1-2.0 |
| 12. | Purified Water | q.s. |
| 13. | Hypromellose | 1-5 |
| 14. | Polyethylene Glycol | 0.1-5 |
| 15. | Isopropyl Alcohol | q.s. |
| 16. | Purified water | q.s. |
| 17. | Dutasteride | 0.1-0.5 |
| 18. | Butylated hydroxy toluene | 0.01-2.0 |
| 19. | Povidone | 1-5 |
| 20. | Polyoxyl 40 hydrogenated castor oil | 0.1-0.5 |
| 21. | Isopropyl Alcohol | q.s. |
| 22. | Hypromellose | 0.5-5 |
| 23. | Triethyl Citrate | 0.1-0.5 |
| 24. | Purified Talc | 0.1-2.0 |
| 25. | Titanium dioxide | 0.1-5.0 |
| 26. | Yellow Oxide of Iron | 0.01-2.0 |
| 27. | Isopropyl Alcohol | q.s. |
| 28. | Purified water | q.s. | b) Manufacturing Procedure for Tamsulosin HCl and Dutasteride Pellets

Stage I: Dry mixed Tamsulosin, MCCI, BHT and PG for suitable time, granulated and prepared drug pellets by using the extrusion, i.e., prepared the wet mass using binder solution and passed through extruder by using suitable screen.

Stage II: Loaded extrudes into the Spheronizer, and spheronized the extrude.

Stage III: Dried the pellets into FLP. After drying, sift the pellets through a suitable screen.

Stage IV: The dried pellets were coat with Methacrylic Acid—Ethyl Acrylate Copolymer, Triethyl citrate and Purified Talc.

Stage V: Taken Isopropyl Alcohol and dispersed Hypromellose into it then added Purified Water. Stirred the solution with the help of stirrer continuously, till the solution get clear then added PEG and stirred well, coated the same solution over the Tamsulosin HCl coated pellets.

Stage VI: Drug Layering Solution: Taken required quantity of Isopropyl alcohol and dispersed Dutasteride into it with the help of stirrer, then added Povidone, Butylated Hydroxy Toluene, Polyoxyl 40 hydrogenated castor oil. Stirred the solution with help of stirrer to form homogenous dispersion, and coated over the above seal coated pellets.

Stage VII: Taken Isopropyl alcohol and dispersed Hypromellose in to it, and then added Purified water, stirred the solution, then added Triethyl Citrate, Purified Talc, Titanium dioxide, and Yellow Oxide of Iron. Stirred the solution with the help of stirrer to get homogenous dispersion, and coated the pellets.

Example 2

Tamsulosin HCl 0.4/Dutasteride 0.5 mg Capsule Formulation Strategy a) Composition of Tamsulosin Hydrochloride and Dutasteride Pellets

| Sr. No. | Ingredients | % (Range) |
|---|---|---|
| 1. | Tamsulosin Hydrochloride | 0.1-0.5 |
| 2. | Microcrystalline Cellulose | 50-95 |
| 3. | Butylated Hydroxy Toluene | 0.1-0.5 |
| 4. | Propyl Gallate | 0.1-0.5 |
| 5. | Methacrylic Acid and Ethyl Acrylate Copolymer | 1-20 |
| 6. | Triethyl Citrate | 0.1-5.0 |
| 7. | Polysorbate 80 | 0.1-0.5 |
| 8. | Purified Water | q.s. |
| 9. | Methacrylic Acid and Ethyl Acrylate Copolymer | 1-20 |
| 10. | Triethyl Citrate | 0.1-0.5 |
| 11. | Purified Talc | 0.1-2.0 |
| 12. | Purified Water | q.s. |
| 13. | Hypromellose | 1-5 |
| 14. | Polyethylene Glycol | 0.1-5 |
| 15. | Silicon Dioxide | 0.1-2.0 |
| 16. | Isopropyl Alcohol | q.s. |
| 17. | Purified water | q.s. |
| 18. | Dutasteride | 0.1-0.5 |
| 19. | Butylated hydroxy toluene | 0.01-2.0 |
| 20. | Povidone | 1-5 |
| 21. | Polyoxyl 40 hydrogenated castor oil | 0.1-0.5 |
| 22. | Medium chain Triglyceride | 0.1-0.5 |
| 23. | Silicon Dioxide | 0.1-2.0 |
| 24. | Isopropyl Alcohol | q.s. |
| 25. | Hypromellose | 0.5-5 |
| 26. | Triethyl Citrate | 0.1-0.5 |
| 27. | Purified Talc | 0.1-2.0 |
| 28. | Titanium dioxide | 0.1-5.0 |
| 29. | Isopropyl Alcohol | q.s. |
| 30. | Purified water | q.s. | b) Manufacturing Procedure for Tamsulosin HCl and Dutasteride Pellets

Stage I: Dry mixed Tamsulosin, MCC, BHT and PG for suitable time, granulated and prepared drug pellets by using the extrusion, i.e., prepared the wet mass using binder solution and passed through extruder by using suitable screen.

Stage II: Loaded extrudes into the Spheronizer and spheronized the extrude.

Stage III: Dried the pellets into FLP. After drying sift the pellets through a suitable screen.

Stage IV: The dried pellets were coat with Methacrylic Acid—Ethyl Acrylate Copolymer, Triethyl citrate and Purified Talc.

Stage V: Taken Isopropyl Alcohol and dispersed Hypromellose into it then added Purified Water, Stirred the solution with the help of stirrer continuously, till the solution get clear then added PEG, silicon dioxide and stirred well. Coated the same solution over the Tamsulosin HCl coated pellets.

Stage VI: Drug Layering Solution: Taken required quantity of Isopropyl alcohol and dispersed Dutasteride into it with the help of stirrer, then added Povidone, Butylated Hydroxy Toluene, Polyoxyl 40 hydrogenated castor oil, Medium chain Triglyceride and silicon dioxide. Stirred the solution with help of stirrer to form homogenous dispersion, and coated over the above seal coated pellets.

Stage VII: Taken Isopropyl alcohol and dispersed Hypromellose in to it and then added Purified water, stirred the solution, then added Triethyl Citrate, Purified Talc, Titanium dioxide, and Yellow Oxide of Iron stir the solution with the help of stirrer to get homogenous dispersion, and coated the pellets.

We claim:

1. A multiparticulate formulation comprising:
a) an inner core of Tamsulosin hydrochloride present in a range of 0.1-0.5%, wherein the inner core is coated with a modified release coating, wherein the modified release coating is coated with a first seal coating; and
b) an outer coating layer of Dutasteride present in a range of 0.1-0.5%, wherein the outer coating layer is coated with a second seal coating,
wherein each particulate of the multiparticulate formulation has a single unit comprising the inner core of tamsulosin and the outer coating layer of dutasteride,
wherein the modified release coating comprises:
a release modifying agent in a range of 1-20 wt %;
a plasticizer in a range of 0.1-0.5 wt %;
an anti-tacking agent in a range of 0.1-2.0 wt %;
a processing solvent; and
optionally, one or more pharmaceutically acceptable excipients(s), and
wherein the multiparticulate formulation is filled in a hard gelatin capsule or compressed in a tablet form.

2. The formulation as claimed in claim 1, wherein the inner core comprises:
a) Tamsulosin hydrochloride;
b) a diluent;
c) an antioxidant;
d) a binder solution; and
e) optionally, one or more pharmaceutically acceptable excipients(s).

3. The formulation as claimed in claim 2, wherein the binder solution comprises:
a) a release modifying agent;
b) a plasticizer;
c) a surfactant;
d) a processing solvent; and
e) optionally, one or more pharmaceutically acceptable excipients(s).

4. The formulation as claimed in claim 1, wherein the first seal coating comprises:
a) a seal coating polymer;
b) a plasticizer;
c) one or more processing solvent(s); and
d) optionally, one or more pharmaceutically acceptable excipients(s).

5. The formulation as claimed in claim 1, wherein the outer coating layer comprises:
a) Dutasteride;
b) an antioxidant;
c) a binder;
d) an emulsifying agent;
e) a processing solvent; and
f) optionally, one or more pharmaceutically acceptable excipients(s).

6. The formulation as claimed in claim 1, wherein the second seal coating comprises:
a) a seal coating polymer;
b) a plasticizer;
c) an anti-tacking agent;
d) an opacifier;
e) a colouring agent;
f) a processing solvent; and
g) optionally, one or more pharmaceutically acceptable excipients(s).

7. The formulation as claimed in claim 1, wherein the formulation is in a form of pellets, granules or extrudates.

8. A process for the preparation of a multiparticulate formulation, comprising the step of:
a) preparing an inner core of Tamsulosin;
b) coating a modified release polymer coating dispersion on said inner core to obtain a modified release inner core;

c) coating said modified release inner core with first seal coating solution to obtain a first seal coated inner core;

d) coating the first seal coated inner core with outer coating dispersion of dutasteride to obtain a dutasteride coated inner core in the form of the multiparticulate formulation;

e) coating said dutasteride coated inner core with a second sealcoating dispersion to obtain the multiparticulate formulation, wherein the modified release polymer coating comprises:
a release modifying agent in a range of 1-20 wt %;
a plasticizer in a range of 0.1-0.5 wt %;
an anti-tacking agent in a range of 0.1-2.0 wt %;
a processing solvent; and
optionally, one or more pharmaceutically acceptable excipients(s), and wherein the multiparticulate formulation is filled in a hard gelatin capsule or compressed in a tablet form.

9. The process as claimed in claim 8, wherein preparing the inner core of Tamsulosin comprises the step of:
   i) dry mixing tamsulosin with at least one diluent and at least one antioxidant and/or one or more pharmaceutically acceptable excipient(s) to obtain a mixture;
   ii) preparing a wet mass of said mixture with a binder solution;
   iii) granulating or pelleting or extruding said wet mass to obtain granules or pellets or extrudates;
   iv) spheronizing said granules or pellets or extrudates to obtain spheronized granules or pellets or extrudates;
   v) drying the spheronized granules or pellets or extrudates.

10. The process as claimed in claim 8, wherein the modified release coating dispersion preparation process comprises of:
dispersing the release modifying agent, plasticizer and anti-tacking agent, optionally one or more pharmaceutically acceptable excipient(s) in a processing solvent to obtain a homogenous dispersion for the modified release coating.

11. The process as claimed in claim 8, wherein the first seal coating solution preparation process comprises of:
   i) dispersing a sealcoating polymer in a first processing solvent followed by addition of a second processing solvent;
   ii) stirring said dispersion continuously to obtain a clear solution;
   iii) adding a plasticizer, optionally one or more pharmaceutically acceptable excipient(s) to said clear solution to obtain a first seal coating solution.

12. The process as claimed in claim 8, wherein the outer coating dispersion preparation process comprises of:
   i) dispersing Dutasteride in a first processing solvent with continuous stirring;
   ii) adding a binder, antioxidant, solubilizer, anti-tacking, emulsifying agent, and optionally one or more pharmaceutically acceptable excipient(s) to said dispersion to obtain a homogenous outer coating dispersion.

13. The process as claimed in claim 8, wherein the second seal coating dispersion preparation process comprises of:
   i) dispersing a seal coating polymer in a first processing solvent followed by addition of a second processing solvent; and
   ii) adding a plasticizer, anti-tacking agent, opacifier, coloring agent, optionally one or more pharmaceutically acceptable excipient(s) with continuous stirring to obtain a homogenous second seal coating dispersion.

* * * * *